United States Patent
Bisconte de Saint Julien et al.

(10) Patent No.: US 7,316,897 B2
(45) Date of Patent: Jan. 8, 2008

(54) PROCESS, DEVICE AND REAGENT FOR CELL SEPARATION

(75) Inventors: Jean-Claude Bisconte de Saint Julien, Saint Laurent de Cerdans (FR); Patricia Paterlini, Paris (FR)

(73) Assignees: L'Institut National de la Sante et de la Recherche Medicale (INSERM) (FR); L'Assistance Publique, Hopitaux de Paris (AP-HP) (FR); L'Universite Rene Descartes Paris 5 (FR)

( * ) Notice: Subject to any disclaimer, the term of this patent is extended or adjusted under 35 U.S.C. 154(b) by 0 days.

(21) Appl. No.: 09/790,673

(22) Filed: Feb. 22, 2001

(65) Prior Publication Data

US 2002/0028431 A1 Mar. 7, 2002

Related U.S. Application Data

(63) Continuation of application No. PCT/FR99/01976, filed on Aug. 23, 1999.

(30) Foreign Application Priority Data

Aug. 25, 1998 (FR) .................................. 98 10696

(51) Int. Cl.
*A01N 1/00* (2006.01)
*C12N 5/08* (2006.01)

(52) U.S. Cl. .......................... 435/2; 435/366; 435/371; 435/372

(58) Field of Classification Search .................. 436/17, 436/18, 64, 177; 435/2, 6, 173.7, 5, 7.23, 435/366, 371, 372
See application file for complete search history.

(56) References Cited

U.S. PATENT DOCUMENTS

| | | | |
|---|---|---|---|
| 4,581,331 A * | 4/1986 | Richards et al. .............. 435/29 |
| 4,751,179 A | 6/1988 | Ledis et al. | |
| 5,057,413 A * | 10/1991 | Terstappen et al. ........... 435/29 |
| 5,070,014 A * | 12/1991 | Dorn ....................... 435/307.1 |
| 5,498,336 A * | 3/1996 | Katsurada et al. .......... 210/496 |
| 5,516,695 A * | 5/1996 | Kim et al. .................... 436/17 |
| 5,532,139 A | 7/1996 | Miller | |
| 5,648,222 A * | 7/1997 | Tse et al. ................... 435/7.23 |
| 5,688,649 A * | 11/1997 | Croce et al. .................... 435/6 |
| 6,139,757 A * | 10/2000 | Ohmura et al. ............. 210/797 |
| 6,190,855 B1 * | 2/2001 | Herman et al. ................ 435/2 |
| 6,265,229 B1 * | 7/2001 | Fodstad et al. ............. 436/526 |
| 6,365,362 B1 * | 4/2002 | Terstappen et al. ......... 209/213 |

FOREIGN PATENT DOCUMENTS

| | | |
|---|---|---|
| DE | 28 08 039 A1 | 8/1978 |
| EP | 0 277 837 B1 | 8/1988 |
| WO | WO 91/04318 | 4/1991 |
| WO | WO 95/24648 * | 9/1995 |

OTHER PUBLICATIONS

Rostagno, P. et al., Detection of rare circulating breast cancer cells by filtration cytometry and identification by DNA content: Sensitivity in an experimental model, 1997, Anticancer research, 17(4A):2481-2485.*

Fox et al., "Formaldehyde fixation", Aug. 1985, The journal of histochemistry and cytochemistry, vol. 33, Issue 8, pp. 845-853.*

Assa et al., "The effect of alfalfa saponins on growth and lysis of *Physarum polycephalum*", Jan. 1975, Archives of Microbiology, vol. 103, No. 1, pp. 77-81.*

C.H. Zierdt et al., *Development of a Lysis-Fitration Blood Culture Technique*, Journal of Clinical Microbiology, vol. 5, No. 1, 1977, pp. 46-50.

* cited by examiner

*Primary Examiner*—Mark L. Shibuya
(74) *Attorney, Agent, or Firm*—DLA Piper US LLP

(57) ABSTRACT

A cell separation process for the isolation of pathogenic cells in a small concentration in a biological fluid specimen, including treating the biological specimen to modify in a differential manner selected rare cells and other cells and causing differential migration of cells that reacted during treatment versus cells that did not react during treatment.

19 Claims, No Drawings

PROCESS, DEVICE AND REAGENT FOR CELL SEPARATION

RELATED APPLICATION

This is a continuation of International Application No. PCT/FR99/01976, with an international filing date of Aug. 23, 1999, which is based on French Patent Application No. 98/10696, filed Aug. 25, 1998.

FIELD OF THE INVENTION

The present invention pertains to the field of the detection of cancerous cells circulating in a biological fluid, especially in the blood or in the cerebrospinal fluid.

BACKGROUND

The invention pertains more specifically to the detection of pathological cells such as micrometastases which can diffuse spontaneously after a surgical intervention, especially after the ablation of a cancerous organ, or of lymphocyte cells infected by viruses.

The early detection of micrometastases makes it possible to evaluate the risks of dissemination and onset of secondary cancers. The difficulty in the detection of such micrometastases stems from the small amount of cells present in a blood specimen.

The early detection of lymphocytes infected by viruses enables indirect and early detection of viral diseases.

In order to separate such rare events, it has been proposed in the prior art to first perform cell labeling. Specifically, it has been proposed to specifically affix the cancerous cells to magnetic balls. Use has also been made of cell sorters or the PCR (Polymerase Chain Reaction) method. These methods are time consuming and can not be routinely performed.

Also proposed in PCT patent WO 91/014318 was a process for the separation of different living cells, such as pancreas islet cells and acinar cells, using a composition comprising a metabolically inert water-soluble substance which regulates the density, osmolarity and pH, a physiological cold storage solution containing viscosity modifiers that increase the viscosity and impermeability agents with osmotic action that destroy the edemas induced by the cold, all contained in a medium capable of maintaining the viability of the cells. The solutions are combined to form a first solution having a density greater that that of the two types of cells in their natural state but lower than that of the second type of cells after incubation in this solution, as well as a second solution having a density lower than that of the two types of cells. Separation is produced by allowing the system to remain in the resting state or by performing centrifugation.

C. H. Zierdt described in "Development of a lysis-filtration blood culture technique", Journal of Clinical Microbiology, Vol. 5, No. 1 1977, pages 46-50, a culture system that retains cells on filtration membranes. The biological specimen is subjected to the action of a lysis solution. The filter is then washed in order to recover the cells retained by the filter.

U.S. Pat. No. 4,751,179 describes a method for the determination of different populations of leukocytes in the blood.

Such solutions are relatively difficult to implement because of the various artifacts inherent in these processes. One of the problems stems, for example, from the agglomeration of balls and the masking of the cells fixed on the balls, by the excess balls. This method is therefore not applicable in a satisfactory manner because it impedes access to the morphology of the cells.

SUMMARY OF THE INVENTION

The goal of the invention is to resolve these disadvantages by proposing a process that is easy to implement, is more reliable than the methods of the prior art and enables confirmation of the diagnosis by access to the cell morphology in the manner to which anatomical pathologists are accustomed.

In its most general sense, the invention envisages a separation process and, in particular, a process for the detection of rare cells. The process comprises treating the biological specimen in order to modify in a differential manner the rare cells that are being targeted on the one hand and the other cells on the other hand, and of providing for a differential migration of the cells that reacted with the reagent versus the cells that did not react with the reagent.

For this purpose, the invention pertains to a cell separation process for the isolation of pathogenic cells present in a very small concentration in a biological fluid sample, characterized in that the specimen is first filtered with a filter having a pore size between 5 and 10 µm.

DETAILED DESCRIPTION

In the context of the present patent, the term "biological fluid" is understood to mean blood and its derivatives (plasma, serum) as well as cerebrospinal fluid, lymph fluid and articular fluid.

In the context of the present patent, the term "pathogenic cells" is understood to refer to cells present in an abnormal state indicative of a disease, and in particular:
 epithelial cells,
 endothelial cells,
 micrometastases,
 cells infected by a virus.

As an example, the invention makes it possible to detect micrometastases in a blood specimen, or cells infected by the hepatitis B or C virus in a biological fluid, or infected cells in a cerebrospinal fluid specimen.

Filtration of the specimen is preferably performed with a filter with a pore size of approximately 8 µm.

According to a preferred mode of implementation, prior to implementation of the filtration step, a specimen-preparation step is performed which comprises adding to the blood specimen a reagent for the lysis of the red cells and differential hardening of the cells foreign to the blood. The function of this reagent is to protect the nucleated blood cells by preserving their deformability and to rigidify the foreign cells, especially the cytokeratin-rich cells.

Thus, because of their flexibility, the blood cells can pass through the filter, despite a nominal section larger than the pore size of the filter, due to deformation of the membrane. The other cells are retained by the filter, even if their dimensions are comparable to those of the target cells, due to the rigidification of the membrane.

According to a preferred variant, a reagent is added to the blood specimen; it is composed of EDTA, bovine serum albumin, saponin, formaldehyde and PBS.

The process advantageously includes a specimen-preparation step consisting of adding to one blood specimen unit nine units of reagent for lysis of the red cells and fixation of the nucleated cells, and in that this preparation is allowed to incubate for approximately 15 minutes.

According to a preferred mode of implementation, the filtration is performed under a partial vacuum of approximately 50,000 Pa.

According to another advantageous variant, agitation of the specimen is performed above the filter.

The invention pertains in particular to a process for the detection of cells capable of being present in a very low concentration in a biological fluid specimen, characterized in that it comprises the steps consisting of:
  reacting a reagent specific to the particles to be detected or, to the contrary, specific to the particles normally present in the biological specimen and capable of masking the presence of the targeted cells, in a manner such as to modify the physical properties of the cells that reacted;
  performing an enrichment of a part of the specimen by a physical selection process ensuring the differential migration of the particles that reacted with the reagent versus the particles that did not react;
  performing the visualization of the possible presence of the targeted particles in the part of the specimen enriched in targeted particles.

According to one particular mode of implementation, a reagent is reacted which modifies the relative deformability of the targeted cells in relation to the deformability of the cells capable of masking the targeted cells.

The invention also pertains to a reagent for cell separation, characterized in that it comprises a detergent capable of degrading the lipid membrane of the red cells and a fixative that is capable of hardening the membrane of the nucleated cells.

The reagent advantageously contains at least some of the following products: EDTA, BSA, saponin, formaldehyde and PBS, or the equivalents of these products.

According to one particular mode of implementation, the reagent according to the invention is constituted by 372 mg of EDTA, 1 g of BSA, 1.75 g of saponin, 10 ml of 37% formaldehyde solution and a sufficient amount of PBS so as to yield 1 liter of reagent.

The invention also pertains to a device for the detection of cancerous cells in a blood specimen, characterized in that it comprises a filtration membrane with a pore size between 5 and 10 μm, and preferably with a pore size of approximately 8 μm.

According to a preferred variant, the device according to the invention has means for creating a flow essentially tangential to the surface of the filter.

The device furthermore preferably has means for creating a partial vacuum of approximately 50,000 Pa under the filter.

In addition, the device for the counting of isolated cells comprises a filter with a pore size of approximately 8 microns and a means for image analysis of the filtrate.

The device makes possible the selection and the individual collection of cells for the purpose of subsequent characterization (for example, by means of PCR) and it comprises a filter with a pore size adapted to the size of the target cells.

The invention also pertains to the application of the separation process for the detection of micrometastases in a blood specimen, for the detection of cells infected by a virus in a biological fluid, for the detection of cells infected by a virus in a cerebrospinal fluid specimen or for diagnosis and monitoring of relapses of cancerous or viral diseases.

The invention makes possible the rapid detection of infections in immunodepressed patients by cell separation from a cerebrospinal fluid specimen as well as the detection and monitoring of cancerous or viral diseases.

The invention will be described below as a nonlimitative example.

A 5-ml whole blood specimen is taken shortly after collection of the blood sample.

Then 45 ml of reagent is added to this specimen and it is allowed to rest for 15 minutes.

According to one variant of implementation, the reagent is composed as follows:
  372 mg of EDTA, marketed by the SIGMA company under reference E5134,
  1 g of BSA Fraction V (bovine serum albumin) marketed by the SIGMA company under reference E4503,
  1.75 g of saponin marketed by the FLUKA company under reference 84510,
  10 ml of 37% formaldehyde solution marketed by the MERCK company under reference 4003,
  QSP of PBS.

The pH is adjusted to 7.2.

The PBS is prepared as follows:
  8 g of sodium chloride,
  0.2 g of potassium chloride,
  2.3 g of disodium hydrogen phosphate,
  0.2 g of potassium dihydrogen phosphate.

After incubation for approximately 15 minutes at ambient temperature, this preparation is filtered on a polycarbonate film with pores approximately 8 μm in section. The filter is subjected to a partial vacuum on the order of 50,000 Pa.

The filtration is performed by means of a device having a vessel in which is placed the blood and reagent preparation. The bottom of this vessel is formed by a filter. According to one variant, a rotor is positioned inside the vessel. It forms a flow tangential to the surface of the filter so as to cause the detachment of the cells and prevent the clogging of the filter during filtration.

Rinsing is then performed with 5 ml of a 0.9% solution of sodium chloride with a pH of 7.

The impact is dyed with 1 ml of 0.025% acridine at pH 6.6 (citrate buffer) or with 1 ml of 40 μg/ml propidium iodide (NaCl buffer) for 10 minutes. During the dyeing process, the filter forming the bottom of the vessel is blocked so as to prevent perfusion of the liquid. The filter is then rinsed with 1 ml of citrate buffer at pH 3.

The cells isolated in this manner can then be the object of a counting by means of an imaging system, microscopy or by a broad-field photon counting system.

The cells can also be recovered by PCR amplification of the DNA of the isolated cells.

The isolated cells can be labeled or be the object of a selective hybridization by a specific PNA (Peptide Nucleic Acids) type reagent or by monoclonal antibodies.

The invention was described above as a nonlimitative example.

The invention claimed is:

1. A cell separation process for isolating at least one of target cells selected from the group consisting of epithelial cells, endothelial cells, micrometastases and cells infected by a virus in small concentration in a blood specimen, comprising:
  chemically treating the blood specimen with a reagent to modify relative deformability of the target cells;
  adding to the blood specimen a reagent for lysis of red cells and fixation of nucleated cells; and
  separating the target cells by filtration with a filter with a pore size between 5 and 10 μm of the blood specimen based on the lack of deformability of the rigidified target cells versus cells that maintained deformability during chemical treatment.

2. The cell separation process according to claim 1, wherein filtration of the blood specimen is performed with a filter with a pore size of approximately 8 μm.

3. A cell separation process for isolating cells selected from the group consisting of epithelial cells, endothelial cells, micrometastases and cells infected by a virus in small concentration in a blood specimen, comprising:
   chemically treating the blood specimen with a reagent to modify relative deformability of the target cells; and
   separating the target cells by filtration with a filter with a pore size between 5 and 10 μm of the blood specimen based on the lack of deformability of the rigidified target cells versus cells that maintained deformability during chemical treatment,
   and wherein the reagent comprises EDTA, bovine serum albumin, saponin, formaldehyde and PBS.

4. A cell separation process for isolating at least one of target cells selected from the group consisting of epithelial cells, endothelial cells, micrometastases and cells infected by a virus in small concentration in a blood specimen, comprising:
   chemically treating one unit of blood specimen with a reagent to modify relative deformability of the target cells;
   adding to one blood specimen nine units of reagent for lysis of red cells and fixation of nucleated cells, and incubating the resulting preparation for approximately 15 minutes; and
   separating the target cells by filtration with a filter with a pore size between 5 and 10 μm of the blood specimen based on the lack of deformability of the rigidified target cells versus cells that maintained deformability during chemical treatment 5. The cell separation process according to any of claims 4, wherein the target cells are micrometastatic cells.

6. The cell separation process according to any of claims 1-4, wherein the target cells are cells infected by a virus.

7. The cell separation process according to any of claims 1-4, wherein filtration of the blood specimen is performed on a polycarbonate film.

8. A cell separation process for isolating at least one of target cells selected from the group consisting of epithelial cells, endothelial cells, micrometastases and cells infected by a virus in small concentration in a blood specimen, comprising:
   chemically treating the blood specimen with a reagent to modify relative deformability of the target cells; and
   separating the target cells by filtration of the blood specimen based on the lack of deformability of the target cells versus cells that maintained deformability during chemical treatment, wherein filtration of the blood specimen is performed with a filter subjected to a partial vacuum on the order of 50,000 Pa.

9. The cell separation process of claim 8, wherein the target cells are cytokeratin-rich cells.

10. A cell separation process for isolating at least one of target cells selected from the group consisting of epithelial cells, endothelial cells, micrometastases and cells infected by a virus in small concentration in a biological fluid specimen, comprising:
   chemically treating the biological fluid specimen with a reagent to modify relative deformability of the target cells; and
   separating the target cells by filtration with a filter with a pore size between 5 and 10 μm of the biological fluid specimen based on the lack of deformability of the rigidified target cells versus cell's that maintained deformability during chemical treatment,
   wherein the target cells are cytokeratin-rich cells or virus-infected cells, and the biological fluid sample is other than a blood sample, and wherein the reagent comprises EDTA, bovine serum albumin, saponin, formaldehyde and PBS.

11. The cell separation process of claim 10, wherein the biological fluid sample comprises cerebrospinal fluid, lymph fluid or articular fluid.

12. The cell separation process according to claim 10, wherein said separation is caused by filtration of the biological fluid specimen with a filter with a pore size between 5 and 10 μm.

13. The cell separation process according to claim 10, wherein filtration of the biological fluid specimen is performed with a filter with a pore size of approximately 8 μm.

14. The cell separation process of claim 10, wherein filtration of the biological fluid specimen is performed on a polycarbonate film.

15. A cell separation process for isolating at least one of target cells selected from the group consisting of epithelial cells, endothelial cells, micrometastases and cells infected by a virus in small concentration in a biological fluid specimen, comprising:
   chemically treating the biological fluid specimen with a reagent to modify relative deformability of the target cells; and
   separating the target cells by filtration with a filter with a pore size between 5 and 10 μm of the biological fluid specimen based on the lack of deformability of the rigidified target cells versus cells that maintained deformability during chemical treatment,
   wherein the target cells are cytokeratin-rich cells or virus-infected cells, and the biological fluid sample is other than a blood sample, and wherein filtration of the biological fluid specimen is performed with a filter subjected to a partial vacuum on the order of 50,000 Pa.

16. The cell separation process of claim 15, wherein the biological fluid sample comprises cerebrospinal fluid, lymph fluid or articular fluid.

17. The cell separation process according to claim 15, wherein said separation is caused by filtration of the biological fluid specimen with a filter with a pore size between 5 and 10 μm.

18. The cell separation process according to claim 15, wherein filtration of the biological fluid specimen is performed with a filter with a pore size of approximately 8 μm.

19. The cell separation process of claim 15, wherein filtration of the biological fluid specimen is performed on a polycarbonate film.

* * * * *